(12) United States Patent
Bryan et al.

(10) Patent No.: US 7,498,036 B2
(45) Date of Patent: Mar. 3, 2009

(54) OPTIMIZED EXPRESSION OF HPV 58 L1 IN YEAST

(75) Inventors: Janine T. Bryan, Furlong, PA (US); Michelle K. Brownlow, Jamison, PA (US); Loren D. Schultz, Harleysville, PA (US); Xin-Min Wang, Schwenksville, PA (US); Kathrin U. Jansen, Doylestown, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/579,111

(22) PCT Filed: Nov. 10, 2004

(86) PCT No.: PCT/US2004/037372
§ 371 (c)(1),
(2), (4) Date: May 11, 2006

(87) PCT Pub. No.: WO2005/047315
PCT Pub. Date: May 26, 2005

(65) Prior Publication Data
US 2007/0036824 A1   Feb. 15, 2007

Related U.S. Application Data

(60) Provisional application No. 60/519,211, filed on Nov. 12, 2003.

(51) Int. Cl.
*A61K 39/12* (2006.01)
(52) U.S. Cl. ................. 424/204.1; 435/91.1
(58) Field of Classification Search .......... 424/204.1, 424/199.1; 435/91.1
See application file for complete search history.

(56) References Cited

U.S. PATENT DOCUMENTS

| | | | |
|---|---|---|---|
| 5,821,087 A | 10/1998 | Lowe et al. | |
| 6,159,729 A | 12/2000 | Hofmann et al. | |
| 2007/0053922 A1* | 3/2007 | Sette et al. | 424/186.1 |

FOREIGN PATENT DOCUMENTS

| | | |
|---|---|---|
| WO | WO 98/34640 | 8/1998 |
| WO | WO 99/02694 | 1/1999 |
| WO | WO 00/09157 | 2/2000 |
| WO | WO 01/14416 A2 | 3/2001 |
| WO | WO 02/08435 A1 | 1/2002 |
| WO | WO 2004/084831 A2 | 10/2004 |
| WO | WO 2005/032586 | 4/2005 |

OTHER PUBLICATIONS

Matsukura et al, Virology, 1990, vol. 177, pp. 833-836.*
Bosch, et al., "The casual relation between human papillomavirus and cervical cancer", J. Clin. Path., vol. 55, pp. 244-265, 2002.
Breitburd, et al., "Immunization with Viruslike Particles from Cottontail Rabbit Papillomavirus (CRPV) Can Protect against Experimental CRPV Infection", J. of Virol., vol. 69, No. 6, Jun. 1995, pp. 3959-3963.
GenBank Accession No. NC_001443.
Guo, et al., "Signals Sufficient for 3'-End Formation of Yeast mRNA", Mol and Cell Biology, vol. 16, No. 6, pp. 2772-2776, Jun. 1996.
Guo, et al., "3'-end-forming signals of yeast mRNA", TIBS 21, pp. 477-481.
Heidmann, et al., "Flexibility and Interchangeability of Polyadenylation Signals in *Saccharomyces cerevisiae*", Mol. and Cell Biology, vol. 14, No. 7, 1994, pp. 4633-4642.
Henikoff, et al., "Transcription Terminates in Yeast Distal to a Control Sequence", Cell., vol. 33, Jun. 1983, pp. 607-614.
Hofmann, et al., "Sequence Determination of Human Papillomavirus Type 6a and Assembly of Virus-Like Particles in *Saccharomyces cerevisiae*", Virology, vol. 209, 1995. pp. 506-518.
Jansen, et al., "Vaccination with yeast-expressed cottontail rabbit papillomavirus (CRPV) virus-like particles protects rabbits from CRPV-induced papillomavirus formation", Vaccine, vol. 13, No. 16, 1995, pp. 1509-1514.
Kirii, et al., "Human Papillomavirus Type 58 DNA Sequence", Virology, vol. 185, 1991, pp. 424-427.
Kotula, et al., "Evaluation of Foreign Gene Codon Optimization in Yeast: Expression of a Mouse IG Kappa Chain", Biotechnology, vol. 9, Dec. 1991, pp. 1386-1389.
Liu, et al., "Polynucleotide viral vaccines: codon optimisation and ubiquitin conjugation enhanced prophylactic and therapeutic efficacy", Vaccine, vol. 20, 2002, pp. 862-869.
McMurray, et al., "Biology of human papillomaviruses", J. Exp. Path., vol. 82, 2001, pp. 15-33.
Russo, et al al., "*Saccharomyces cerevisiae* mRNA 3' End Forming Signals are also Involved in Transcription Termination", Yeast, vol. 11, 1995, pp. 447-453.
Schiffman, et al., "Epidemiologic Evidence Showing That Human Papillomavirus Infection Causes Most Cervical Intraepithelial Neoplasia", J. of National Cancer Inst., vol. 85, vol. 12, 1993, pp. 958-964.
Schiller, et al., "Papillomavirus-Like Particles: Basic and Applied Studies", UK: Leeds Medical Information, 1996, pp. 101-112.
Schiller, et al., "Papillomavirus-Like Particle Vaccines", J. Natl. Cancer Inst. Monographs, No. 28, 2000, pp. 50-54.

(Continued)

*Primary Examiner*—Ali R. Salimi
(74) *Attorney, Agent, or Firm*—Alysia A. Finnegan; Sheldon O. Heber

(57) ABSTRACT

Synthetic DNA molecules encoding the HPV58 L1 protein are provided. Specifically, the present invention provides polynucleotides encoding HPV58 L1 protein, wherein said polynucleotides are codon-optimized for high level expression in a yeast cell. The synthetic molecules may be used to produce HPV58 virus-like particles (VLPs), and to produce vaccines and pharmaceutical compositions comprising the HPV58 VLPs. The vaccines of the present invention provide effective imnunoprophylaxis against papillomavirus infection through neutralizing antibody and cell-mediated immunity and are also useful for treatment of existing HPV infections.

9 Claims, 10 Drawing Sheets

OTHER PUBLICATIONS

Schiller, et al., "Developing HPV virus-like particle vaccines to prevent cervical cancer: a progress report", J. of Clin. Virology., vol. 19, 2000, pp. 67-74.

Sharp, et al., "Synonymous Codon Usage in *Saccharomyces cerevisiae*", Yeast, vol. 7, 1991, pp. 657-678.

Suzich, et al., "Systemic immunization with papillomavirus L1 protein completely prevents the development of viral mucosal papillomas", PNAS USA, vol. 92, Dec. 1995, pp. 11553-11557.

Thalenfeld, et al., "oli 1 Transcripts in Wild Type and in a Cytophasmic 'Petite' Mutant of Yeast*", J. of Biol Chem., vol. 258, No. 23, Dec. 10, 1983, pp. 14065-14065.

Tobery, et al., "Effect of vaccine delivery system on the induction of HPV 16L1-specific humoral and cell-mediated immune responses in immunized rhesus macaques", Vaccine, vol. 21, 2003, pp. 1539-1547.

Zaret, et al., "DNA Sequence Required for Efficient Transcription Termination in Yeast", Cell, vol. 28, Mar. 1982, pp. 563-573.

Zaret, et al., "Mutationally Altered 3' Ends of Yeast CYC1 mRNA Affect Transcript Stability and Translational Efficiency", J. Mol. Biol., vol. 176, 1984, pp. 107-135.

Zhou, et al., "Papillomavirus Capsid Protein Expression Level Depends on the Match Between Codon Usage and tRNA Availability", J. of Virol., vol. 73, No. 6, Jun. 1999, pp. 4972-4982.

* cited by examiner

HPV 58 L1 Nucleotide Sequence Alignment

```
58 L1 wt   (  1)  ATGTCCGTGTGGCGGCCTAGTGAGGCCACTGTGTACCTGCCTCCTGTGCC
58 L1 R    (  1)  ........C...A.A..ATCC...A..T..C..C...T....A..A..T..

58 L1 wt   ( 51)  TGTGTCTAAGGTTGTAAGCACTGATGAATATGTGTCACGCACAAGCATTT
58 L1 R    ( 51)  A..C..C.....C..CTC......C.....C..C..TA.A..CTCT..C.

58 L1 wt   (101)  ATTATTATGCTGGCAGTTCCAGACTTTTGGCTGTTGGCAATCCATATTTT
58 L1 R    (101)  .C..C..C.....TTCC..T...T.G...........T..C.....C..C

58 L1 wt   (151)  TCCATCAAAAGTCCCAATAACAATAAAAAAGTATTAGTTCCCAAGGTATC
58 L1 R    (151)  ........GTC...A..C.....C..G..G..C..G.....A.....C..

58 L1 wt   (201)  AGGCTTACAGTATAGGGTCTTTAGGGTGCGTTTACCTGATCCCAATAAAT
58 L1 R    (201)  T..T..G..A..C..A.....C..A..CA.A..G..A..C..A..C..G.

58 L1 wt   (251)  TTGGTTTTCCTGATACATCTTTTTATAACCCTGATACACAACGTTTGGTC
58 L1 R    (251)  .C.....C..A..C..T..C..C..C.....A..C..T...A.A......

58 L1 wt   (301)  TGGGCATGTGTAGGCCTTGAAATAGGTAGGGGACAGCCATTGGGTGTTGG
58 L1 R    (301)  .....T.....C..TT.G.....C.....A..T..A.............

58 L1 wt   (351)  CGTAAGTGGTCATCCTTATTTCAATAAATTTGATGACACTGAAACCAGTA
58 L1 R    (351)  T..CTC......C..A..C.....C..G..C..C.....C......TCC.

58 L1 wt   (401)  ACAGATATCCCGCACAGCCAGGGTCTGATAACAGGGAATGCTTATCTATG
58 L1 R    (401)  .......C..A..T..A.....T.....C.....A.....T..G..C...

58 L1 wt   (451)  GATTATAAACAAACACAATTATGTTTAATTGGCTGTAAACCTCCCACTGG
58 L1 R    (451)  ..C..C..G.....C.....G.....G..C..T.....G..A..A.....

58 L1 wt   (501)  TGAGCATTGGGGTAAAGGTGTTGCCTGTAACAATAATGCAGCTGCTACTG
58 L1 R    (501)  ...A..C.......G........T........C..C..T........C.

58 L1 wt   (551)  ATTGTCCTCCATTGGAACTTTTTAATTCTATTATTGAGGATGGTGACATG
58 L1 R    (551)  .C.....A.........T.G..C..C..C..C..C..A..C........

58 L1 wt   (601)  GTAGATACAGGGTTTGGATGCATGGACTTTGGTACATTGCAGGCTAATAA
58 L1 R    (601)  ..C..C..T..T..C..T..T........C.....C.....A.....C..
```

FIG. 1A

```
58 L1 wt  ( 651)  AAGTGATGTGCCTATTGATATTTGTAACAGTACATGCAAATATCCAGATT
58 L1 R   ( 651)  GTCC..C..T..A..C..C..C......TCC..C..T..G..C.....C.

58 L1 wt  ( 701)  ATTTAAAAATGGCCAGTGAACCTTATGGGGATAGTTTGTTCTTTTTTCTT
58 L1 R   ( 701)  .C..G..G.....TTC......A..C..T..CTCC........C..CT.G

58 L1 wt  ( 751)  AGACGTGAGCAGATGTTTGTTAGGCACTTTTTTAATAGGGCCGGAAAACT
58 L1 R   ( 751)  ...A.A..A..A.....C..C..A.....C..C..C..A..T..T..GT.

58 L1 wt  ( 801)  TGGCGAGGCTGTCCCGGATGACCTTTATATTAAAGGGTCCGGTAATACTG
58 L1 R   ( 801)  G..T..A.....T..A..C...T.G..C..C..G..T..T.....C..C.

58 L1 wt  ( 851)  CAGTTATCCAAAGTAGTGCATTTTTTTCCAACTCCTAGTGGCTCTATGGTT
58 L1 R   ( 851)  .T..C......TCCTC...T..C..C........ATC...T..C.....C

58 L1 wt  ( 901)  ACCTCAGAATCACAATTATTTAATAAGCCTTATTGGCTACAGCGTGCACA
58 L1 R   ( 901)  .....T.....T.....G..C..C.....A..C...T.G..AA.A..T..

58 L1 wt  ( 951)  AGGTCATAACAATGGCATTTGCTGGGGCAATCAGTTATTTGTTACCGTAG
58 L1 R   ( 951)  ......C.....C..T..C..T.....T..C..A..G..C..C..T..C.

58 L1 wt  (1001)  TTGATACCACTCGTAGCACTAATATGACATTATGCACTGAAGTAACTAAG
58 L1 R   (1001)  .C..C......A.ATC......C.....C..G..T..C.....C..C...

58 L1 wt  (1051)  GAAGGTACATATAAAAATGATAATTTTAAGGAATATGTACGTCATGTTGA
58 L1 R   (1051)  ........C..C..G..C..C..C..C.......C...CA.A..C..C..

58 L1 wt  (1101)  AGAATATGACTTACAGTTTGTTTTTTCAGCTTTGCAAAATTACACTAACTG
58 L1 R   (1101)  G.....C.....G..A..C..C..C..AT.G..T..G..C..CT.G....

58 L1 wt  (1151)  CAGAGATAATGACATATATACATACTATGGATTCCAATATTTTGGAGGAC
58 L1 R   (1151)  .T..A..C.....C..C..C..C..C.....C..T..C..C.....A...

58 L1 wt  (1201)  TGGCAATTTGGTTTAACACCTCCTCCGTCTGCCAGTTTACAGGACACATA
58 L1 R   (1201)  ........C.....G..T..A..A..A.....TTCC..G..A.....C..

58 L1 wt  (1251)  TAGATTTGTTACCTCCCAGGCTATTACTTGCCAAAAAACAGCACCCCCTA
58 L1 R   (1251)  C.....C..C.....T..A.....C..C..T.....G..T..T..A..A.
```

FIG.1B

```
58 L1 wt  (1301)  AAGAAAAGGAAGATCCATTAAATAAATATACTTTTTGGGAGGTTAACTTA
58 L1 R   (1301)  .G..........C.....G..C..G..C..C..C.....A..C.....G

58 L1 wt  (1351)  AAGGAAAAGTTTTCTGCAGATCTAGATCAGTTTCCTTTGGGACGAAAGTT
58 L1 R   (1351)  ...........C.....T..CT.G..C..A..C..A....TA.......

58 L1 wt  (1401)  TTTATTACAATCAGGCCTTAAAGCAAAGCCCAGACTAAAACGTTCGGCCC
58 L1 R   (1401)  C..G..G.....T..TT.G..G..T.....A...T.G..GA.A..T..T.

58 L1 wt  (1451)  CTACTACCCGTGCACCATCCACCAAACGCAAAAAGGTTAAAAAATAA  (SEQ ID NO:3
58 L1 R   (1451)  .A..C..TA.A..T..........GA.A..G.....C..G..G      (SEQ ID NO:1
```

FIG. 1C

Synthetic HPV 58 L1 Nucleotide and Amino Acid Sequences.

```
       M   S   V   W   R   P   S   E   A   T   V   Y   L   P   P   V   P
  1   ATGTCCGTCT GGAGACCATC CGAAGCTACC GTCTACTTGC CACCAGTTCC
      TACAGGCAGA CCTCTGGTAG GCTTCGATGG CAGATGAACG GTGGTCAAGG
       V   S   K   V   V   S   T   D   E   Y   V   S   R   T   S   I   Y
 51   AGTCTCCAAG GTCGTCTCCA CTGACGAATA CGTCTCTAGA ACCTCTATCT
      TCAGAGGTTC CAGCAGAGGT GACTGCTTAT GCAGAGATCT TGGAGATAGA
       Y   Y   A   G   S   S   R   L   L   A   V   G   N   P   Y   F
101   ACTACTACGC TGGTTCCTCT AGATTGTTGG CTGTTGGTAA CCCATACTTC
      TGATGATGCG ACCAAGGAGA TCTAACAACC GACAACCATT GGGTATGAAG
       S   I   K   S   P   N   N   K   K   V   L   V   P   K   V   S
151   TCCATCAAGT CTCCAAACAA CAACAAGAAG GTCTTGGTTC CAAAGGTCTC
      AGGTAGTTCA GAGGTTTGTT GTTGTTCTTC CAGAACCAAG GTTTCCAGAG
       G   L   Q   Y   R   V   F   R   V   R   L   P   D   P   N   K   F
201   TGGTTTGCAA TACAGAGTCT TCAGAGTCAG ATTGCCAGAC CCAAACAAGT
      ACCAAACGTT ATGTCTCAGA AGTCTCAGTC TAACGGTCTG GGTTTGTTCA
       G   F   P   D   T   S   F   Y   N   P   D   T   Q   R   L   V
251   TCGGTTTCCC AGACACTTCC TTCTACAACC CAGACACTCA AAGATTGGTC
      AGCCAAAGGG TCTGTGAAGG AAGATGTTGG GTCTGTGAGT TTCTAACCAG
       W   A   C   V   G   L   E   I   G   R   G   Q   P   L   G   V   G
301   TGGGCTTGTG TCGGTTTGGA AATCGGTAGA GGTCAACCAT TGGGTGTTGG
      ACCCGAACAC AGCCAAACCT TTAGCCATCT CCAGTTGGTA ACCCACAACC
       V   S   G   H   P   Y   F   N   K   F   D   D   T   E   T   S   N
351   TGTCTCTGGT CACCCATACT TCAACAAGTT CGACGACACC GAAACCTCCA
      ACAGAGACCA GTGGGTATGA AGTTGTTCAA GCTGCTGTGG CTTTGGAGGT
       R   Y   P   A   Q   P   G   S   D   N   R   E   C   L   S   M
401   ACAGATACCC AGCTCAACCA GGTTCTGACA ACAGAGAATG TTTGTCCATG
      TGTCTATGGG TCGAGTTGGT CCAAGACTGT TGTCTCTTAC AAACAGGTAC
       D   Y   K   Q   T   Q   L   C   L   I   G   C   K   P   T   G
451   GACTACAAGC AAACCCAATT GTGTTTGATC GGTTGTAAGC CACCAACTGG
      CTGATGTTCG TTTGGGTTAA CACAAACTAG CCAACATTCG GTGGTTGACC
       E   H   W   G   K   G   V   A   C   N   N   A   A   T   D
501   TGAACACTGG GGTAAGGGTG TTGCTTGTAA CAACAACGCT GCTGCTACCG
      ACTTGTGACC CCATTCCCAC AACGAACATT GTTGTTGCGA CGACGATGGC
       C   P   P   L   E   L   F   N   S   I   I   E   D   G   D   M
551   ACTGTCCACC ATTGGAATTG TTCAACTCCA TCATCGAAGA CGGTGACATG
      TGACAGGTGG TAACCTTAAC AAGTTGAGGT AGTAGCTTCT GCCACTGTAC
       V   D   T   G   F   G   C   M   D   F   G   T   L   Q   A   N   K
```

FIG.2A

```
601  GTCGACACTG GTTTCGGTTG TATGGACTTC GGTACCTTGC AAGCTAACAA
     CAGCTGTGAC CAAAGCCAAC ATACCTGAAG CCATGGAACG TTCGATTGTT
      S  D  V   P  I  D  I   C  N  S   T  C  K   Y  P  D  Y
651  GTCCGACGTT CCAATCGACA TCTGTAACTC CACCTGTAAG TACCCAGACT
     CAGGCTGCAA GGTTAGCTGT AGACATTGAG GTGGACATTC ATGGGTCTGA
      L  K  M   A  S  E   P  Y  G  D   S  L  F   F  F  L
701  ACTTGAAGAT GGCTTCTGAA CCATACGGTG ACTCCTTGTT CTTCTTCTTG
     TGAACTTCTA CCGAAGACTT GGTATGCCAC TGAGGAACAA GAAGAAGAAC
      R  R  E  Q   M  F  V   R  H  F   F  N  R  A   G  K  L
751  AGAAGAGAAC AAATGTTCGT CAGACACTTC TTCAACAGAG CTGGTAAGTT
     TCTTCTCTTG TTTACAAGCA GTCTGTGAAG AAGTTGTCTC GACCATTCAA
      G  E  A   V  P  D  D   L  Y  I   K  G  S   G  N  T  A
801  GGGTGAAGCT GTTCCAGACG ACTTGTACAT CAAGGGTTCT GGTAACACCG
     CCCACTTCGA CAAGGTCTGC TGAACATGTA GTTCCCAAGA CCATTGTGGC
      V  I  Q   S  S  A   F  F  P  T   P  S  G   S  M  V
851  CTGTCATCCA ATCCTCTGCT TTCTTCCCAA CTCCATCTGG TTCCATGGTC
     GACAGTAGGT TAGGAGACGA AAGAAGGGTT GAGGTAGACC AAGGTACCAG
      T  S  E  S   Q  L  F   N  K  P   Y  W  L   Q  R  A  Q
901  ACCTCTGAAT CTCAATTGTT CAACAAGCCA TACTGGTTGC AAAGAGCTCA
     TGGAGACTTA GAGTTAACAA GTTGTTCGGT ATGACCAACG TTTCTCGAGT
      G  H  N   N  G  I   C  W  G   N  Q  L   F  V  T  V  V
951  AGGTCACAAC AACGGTATCT GTTGGGGTAA CCAATTGTTC GTCACTGTCG
     TCCAGTGTTG TTGCCATAGA CAACCCCATT GGTTAACAAG CAGTGACAGC
      D  T  T   R  S  T   N  M  T  L   C  T  E   V  T  K
1001 TCGACACCAC TAGATCCACT AACATGACCT TGTGTACCGA AGTCACCAAG
     AGCTGTGGTG ATCTAGGTGA TTGTACTGGA ACACATGGCT TCAGTGGTTC
      E  G  T  Y   K  N  D   N  F  K   E  Y  V   R  H  V  E
1051 GAAGGTACCT ACAAGAACGA CAACTTCAAG GAATACGTCA GACACGTCGA
     CTTCCATGGA TGTTCTTGCT GTTGAAGTTC CTTATGCAGT CTGTGCAGCT
      E  Y  D   L  Q  F  V   F  Q  L   C  K  I   T  L  T  A
1101 GGAATACGAC TTGCAATTCG TCTTCCAATT GTGTAAGATC ACCTTGACTG
     CCTTATGCTG AACGTTAAGC AGAAGGTTAA CACATTCTAG TGGAACTGAC
      E  I  M   T  Y  I   H  T  M  D   S  N  I   L  E  D
1151 CTGAAATCAT GACCTACATC CACACCATGG ACTCTAACAT CTTGGAAGAC
     GACTTTAGTA CTGGATGTAG GTGTGGTACC TGAGATTGTA GAACCTTCTG
      W  Q  F  G   L  T  P   P  P  S   A  S  L   Q  D  T  Y
1201 TGGCAATTCG GTTTGACTCC ACCACCATCT GCTTCCTTGC AAGACACCTA
     ACCGTTAAGC CAAACTGAGG TGGTGGTAGA CGAAGGAACG TTCTGTGGAT
      R  F  V   T  S  Q   A  I  T  C   Q  K  T   A  P  P  K
```

FIG. 2B

```
1251    CAGATTCGTC ACCTCTCAAG CTATCACCTG TCAAAAGACT GCTCCACCAA
        GTCTAAGCAG TGGAGAGTTC GATAGTGGAC AGTTTTCTGA CGAGGTGGTT
          E   K   E    D   P   L    N   K   Y   T    F   W   E    V   N   L
1301    AGGAAAAGGA AGACCCATTG AACAAGTACA CCTTCTGGGA AGTCAACTTG
        TCCTTTTCCT TCTGGGTAAC TTGTTCATGT GGAAGACCCT TCAGTTGAAC
          K   E   K   F    S   A   D    L   D   Q    F   P   L   G    R   K   F
1351    AAGGAAAAGT TCTCTGCTGA CTTGGACCAA TTCCCATTGG GTAGAAAGTT
        TTCCTTTTCA AGAGACGACT GAACCTGGTT AAGGGTAACC CATCTTTCAA
           L   L   Q    S   G   L   K    A   K   P    R   L   K    R   S   A   P
1401    CTTGTTGCAA TCTGGTTTGA AGGCTAAGCC AAGATTGAAG AGATCTGCTC
        GAACAACGTT AGACCAAACT TCCGATTCGG TTCTAACTTC TCTAGACGAG
           T   T   R    A   P   S    T   K   R   K    K   V   K    K   *  (SEQ ID NO:2)
1451    CAACCACTAG AGCTCCATCC ACCAAGAGAA AGAAGGTCAA GAAGTAA (SEQ ID NO:1)
        GTTGGTGATC TCGAGGTAGG TGGTTCTCTT TCTTCCAGTT CTTCATT (SEQ ID NO:10
```

FIG. 2C

Northern Blot of HPV 58 L1 wt and 58 L1 R transcripts.

Transmission EM of VLPs Composed of HPV 58 L1 R Protein Molecules.

US 7,498,036 B2

OPTIMIZED EXPRESSION OF HPV 58 L1 IN YEAST

CROSS-REFERENCE TO RELATED APPLICATIONS

This application is a §371 National Stage Application of PCT/US2004/037372, international filing date of Nov. 10, 2004, which claims the benefit of U.S. Provisional Application No. 60/519,211, filed Nov. 12, 2003, now expired.

FIELD OF THE INVENTION

The present invention relates generally to the prevention and/or therapy of human papillomavirus (HPV) infection. More specifically, the present invention relates to synthetic polynucleotides encoding HPV58 L1 protein, and to recombinant vectors and hosts comprising said polynucleotides. This invention also relates to HPV58 virus-like particles (VLPs), wherein the VLPs are produced by expressing recombinant HPV58 L1 or L1+L2 in yeast cells and to their use in vaccines and pharmaceutical compositions for preventing and treating HPV infections.

BACKGROUND OF THE INVENTION

There are more than 80 types of human papillomavirus (HPV), many of which have been associated with a wide variety of biological phenotypes, from benign proliferative warts to malignant carcinomas (for review, see McMurray et al., *Int. J. Exp. Pathol.* 82(1): 15-33 (2001)). HPV6 and HPV11 are the types most commonly associated with benign warts, nonmalignant condyloma acuminata and/or low-grade dysplasia of the genital or respiratory mucosa. HPV16 and HPV18 are the high-risk types most frequently associated with in situ and invasive carcinomas of the cervix, vagina, vulva and anal canal. More than 90% of cervical carcinomas are associated with infections of HPV16, HPV18 or the less prevalent oncogenic types HPV31, -33, -45, -52 and -58 (Schiffman et al., *J. Natl. Cancer Inst.* 85(12): 958-64 (1993)). The observation that HPV DNA is detected in more than 90% of cervical cancers provides strong epidemiological evidence that HPVs cause cervical carcinoma.

Papillomaviruses are small (50-60 nm), nonenveloped, icosahedral DNA viruses that encode up to eight early and two late genes. The open reading frames (ORFs) of the viral genomes are designated E1 to E7, and L1 and L2, where "E" denotes early and "L" denotes late. L1 and L2 code for virus capsid proteins, while the E genes are associated with functions such as viral replication and cellular transformation.

The L1 protein is the major capsid protein and has a molecular weight of 55-60 kDa. The L2 protein is the minor capsid protein. Immunological data suggest that most of the L2 protein is internal to the L1 protein in the viral capsid. Both the L1 and L2 proteins are highly conserved among different papillomaviruses.

Expression of the L1 protein or a combination of the L1 and L2 proteins in yeast, insect cells, mammalian cells or bacteria leads to self-assembly of virus-like particles (VLPs) (for review, see Schiller and Roden, in *Papilloinavirus Reviews: Current Research on Papillomaviruses*; Lacey, ed. Leeds, UK: Leeds Medical Information, pp 101-12 (1996)). VLPs are morphologically similar to authentic virions and are capable of inducing high titres of neutralizing antibodies upon administration into animals or humans. Because VLPs do not contain the potentially oncogenic viral genome, they present a safe alternative to the use of live virus in HPV vaccine development (for review, see Schiller and Hidesheim, *J. Clin. Virol.* 19: 67-74 (2000)). For this reason, the L1 and L2 genes have been identified as immunological targets for the development of prophylactic and therapeutic vaccines for HPV infection and disease.

HPV vaccine development and commercialization have been hindered by difficulties associated with obtaining high expression levels of capsid proteins in successfully transformed host organisms, limiting the production of purified protein. Therefore, despite the identification of wild-type nucleotide sequences encoding HPV L1 proteins such as HPV58 L1 protein, it would be highly desirable to develop a readily renewable source of crude HPV L1 protein that utilizes HPV58 L1-encoding nucleotide sequences that are optimized for expression in the intended host cell. Additionally, it would be useful to produce large quantities of HPV58 L1 VLPs having the immunity-conferring properties of the native proteins for use in vaccine development.

SUMMARY OF THE INVENTION

The present invention relates to compositions and methods to elicit or enhance immunity to the protein products expressed by HPV58 L1 genes. Specifically, the present invention provides polynucleotides encoding HPV58 L1 protein, wherein the polynucleotides have been codon-optimized for high level expression in a yeast cell. The present invention further provides HPV58 virus-like particles (VLPs), wherein said VLPs are produced by expressing recombinant HPV58 L1 or L1+L2 in yeast cells, and discloses use of HPV58 VLPs in pharmaceutical compositions and vaccines for the prevention and/or treatment of HPV-associated cancer.

The present invention relates to synthetic DNA molecules encoding the HPV58 L1 protein. The codons of the synthetic molecules are designed so as to use the codons preferred by a yeast cell. The synthetic molecules may be used as a source of HPV58 L1 protein, which may self-assemble into VLPs. Said VLPs may be used in a VLP-based vaccine.

An exemplary embodiment of the present invention comprises a synthetic nucleic acid molecule which encodes the HPV58 L1 protein as set forth in SEQ ID NO:2, said nucleic acid molecule comprising a sequence of nucleotides that is codon-optimed for high-level expression in a yeast cell. In preferred embodiments, the nucleic acid comprises a sequence of nucleotides as set forth in SEQ ID NO:1 (designated herein "58 L1 R sequence").

Also provided are recombinant vectors and recombinant host cells, both prokaryotic and eukaryotic, which contain the nucleic acid molecules disclosed throughout this specification. In a preferred embodiment of the present invention, the host cell is a yeast cell.

The present invention also relates to a process for expressing an HPV58 L1 protein in a recombinant host cell, comprising: (a) introducing a vector comprising a nucleic acid encoding an HPV58 L1 protein into a yeast host cell; and (b) culturing the yeast host cell under conditions which allow expression of said HPV58 L1 protein.

The present invention further relates to a process for expressing an HPV58 L1 protein in a recombinant host cell, comprising: (a) introducing a vector comprising a nucleic acid molecule encoding an HPV58 L1 protein into a yeast host cell; wherein the nucleic acid molecule is codon-optimized for optimal expression in the yeast host cell and; (b) culturing the yeast host cell under conditions which allow expression of said HPV58 L1 protein.

In preferred embodiments of this aspect of the invention, the nucleic acid comprises a sequence of nucleotides as set forth in SEQ ID NO:1.

This invention also relates to HPV58 virus-like particles (VLPs) which are produced in yeast cells, methods of producing HPV58 VLPs, and methods of using HPV58 VLPs.

In a preferred embodiment of the invention, the yeast is selected from the group consisting of: *Saccharoinyces cerevisiae, Hansenula polymorpha, Pichia pastoris, Kluyveroinyces fragilis, Kluyveromyces lactis*, and *Schizosaccharomyces pombe*.

Another aspect of this invention is an HPV58 VLP, wherein the VLP is produced by recombinant expression of HPV58 L1 or HPV58 L1+L2 in a yeast cell.

Yet another aspect of this invention is an HPV58 VLP which comprises an HPV58 L1 protein produced by a codon-optimized HPV58 L1 gene. In an exemplary embodiment of this aspect of the invention, the codon-optimized HPV58 L1 gene comprises a sequence of nucleotides as set forth in SEQ ID NO:1.

This invention also provides a method for inducing an immune response in an animal comprising administering HPV58 virus-like particles to the animal. In a preferred embodiment, the HPV58 VLPs are produced by a codon-optimnized gene.

Yet another aspect of this invention is a method of preventing or treating HPV-associated cervical cancer comprising administering to a mammal a vaccine comprising HPV58 VLPs. In a preferred embodiment of this aspect of the invention, the HPV58 VLPs are produced in yeast.

This invention also relates to a vaccine comprising HPV58 virus-like particles (VLPs), wherein the HPV58 VLPs are produced in yeast.

In an alternative embodiment of this aspect of the invention, the vaccine further comprises VLPs of at least one additional HPV type. The at least one additional HPV type may be any HPV type of interest, including any HPV type described in the art or those subsequently identified. In a preferred embodiment, the HPV type is a type that is associated with a clinical phenotype such as warts or cervical cancer. In a furher preferred embodiment, the at least one additional HPV type is selected from the group consisting of: HPV6, HPV11, HPV16, HPV18, HPV31, HPV33, HPV35, HPV39, HPV45, HPV51, HPV52, HPV55, HPV56, HPV59, and HPV68.

This invention also relates to pharmaceutical compositions comprising HPV 58 virus-like particles and a pharmaceutically acceptable carrier, wherein the HPV58 VLPs are produced in yeast. Further, this invention relates to pharmaceutical compositions comprising HPV58 VLPs and VLPs of at least one additional HPV type. In a preferred embodiment, the at least one additional HPV type is selected from the group consisting of: HPV6, HPV11, HPV16, HPV18, HPV31, HPV33, HPV35, HPV39, HPV45, HPV51, HPV52, HPV55, HPV56, HPV59, and HPV68.

As used throughout the specification and in the appended claims, the singular forms "a," "an," and "the" include the plural reference unless the context clearly dictates otherwise.

As used throughout the specification and appended claims, the following definitions and abbreviations apply:

The term "promoter" refers to a recognition site on a DNA strand to which the RNA polymerase binds. The promoter forms an initiation complex with RNA polymerase to initiate and drive transcriptional activity. The complex can be modified by activating sequences termed "enhancers" or "upstream activating sequences" or inhibiting sequences termed "silencers".

The term "vector" refers to some means by which DNA fragments can be introduced into a host organism or host tissue. There are various types of vectors including plasmids, viruses (including adenovirus), bacteriophages and cosmids.

The term "cassette" refers to a nucleotide or gene sequence that is to be expressed from a vector, for example, the nucleotide or gene sequence encoding the HPV58 L1 protein. In general, a cassette comprises a gene sequence inserted into a vector which, in some embodiments, provides regulatory sequences for expressing the nucleotide or gene sequence. In other embodiments, the nucleotide or gene sequence provides the regulatory sequences for its expression. In further embodiments, the vector provides some regulatory sequences and the nucleotide or gene sequence provides other regulatory sequences. For example, the vector can provide a promoter for transcribing the nucleotide or gene sequence and the nucleotide or gene sequence provides a transcription termination sequence. The regulatory sequences which can be provided by the vector include, but are not limited to, enhancers, transcription termination sequences, splice acceptor and donor sequences, introns, ribosome binding sequences, and poly(A) addition sequences.

The designations "58 L1 wild-type sequence" and "58 L1 wt sequence" refer to the HPV58 L1 sequence disclosed herein as SEQ ID NO:3. Although the HPV58 L1 wild-type sequence has been described previously, it is not uncommon to find minor sequence variations between DNAs obtained from clinical isolates. Therefore, a representative 58 L1 wild-type sequence was isolated from clinical samples previously shown to contain HPV58 DNA (see EXAMPLE 1). The 58 L1 wild-type sequence was used as a reference sequence to compare the codon-optimized 58 L1 sequences disclosed herein (see FIG. 1).

The designations "HPV8 L1 R" and "58 L1 R" refer to an exemplary synthetic HPV58 L1 nucleotide sequence (SEQ ID NO:1), disclosed herein, wherein the sequence was rebuilt so that it comprises codons that are preferred for high-level expression by a yeast cell.

The term "effective amount" means sufficient vaccine composition is introduced to produce the adequate levels of the polypeptide, so that an immune response results. One slcilled in the art recognizes that this level may vary.

A "conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

The term "mammalian" refers to any mammal, including a human being.

"VLP" or "VLPs" mean(s) virus-like particle or virus-like particles.

"Synthetic" means that the HPV58 L1 gene was created so that it contains a sequence of nucleotides that is not the same as the sequence of nucleotides present in the designated naturally occurring wild-type HPV58 L1 gene (58 L1 wt, SEQ ID NO:3). As stated above, synthetic molecules are provided herein comprising a sequence of nucleotides comprising codons that are preferred for expression by yeast cells. The synthetic molecules provided herein encode the same amino acid sequences as the wild-type HPV58 L1 gene (SEQ ID NO:2).

BRIEF DESCRIPTION OF THE DRAWINGS

FIG. 1 shows a sequence alignment comparing nucleotides that were altered in the synthetic HPV58 L1 gene of the present invention (SEQ ID NO:1, indicated as "58 L1 R") (See EXAMPLE 2). The reference sequence is the 58 L1 wild-type sequence (SEQ ID NO:3, indicated as "58 L1 wt"; see EXAMPLE 1). Altered nucleotides are indicated at their corresponding location. Nucleotide number is contained within the parentheses. Identical nucleotides in the 58 L1 rebuilt sequence are indicated with dots.

FIG. 2 shows the rebuilt synthetic HPV58 L1 double-stranded nucleic acid and single-code amino acid sequence above. Nucleotide number is indicated to the left.

DETAILED DESCRIPTION OF THE INVENTION

Figure 3:
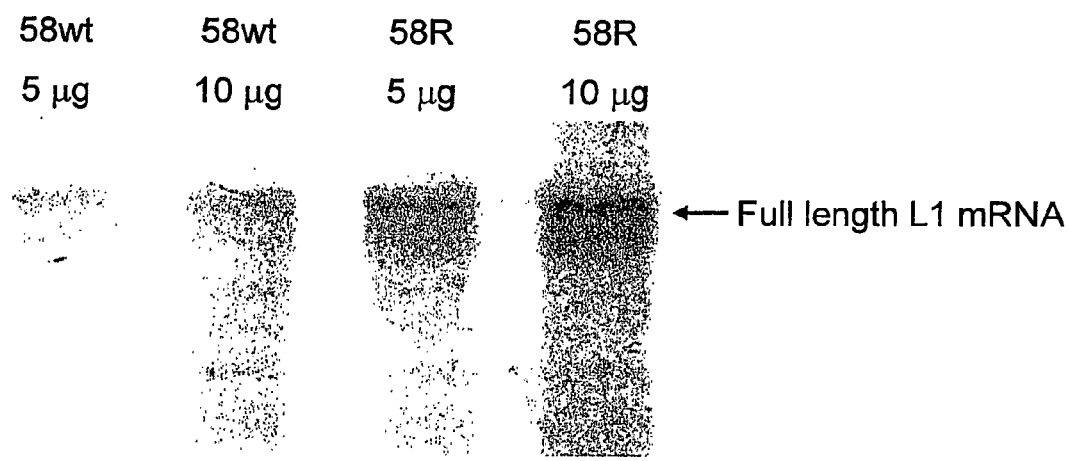
FIG. 3 shows a Northern blot of HPV58 L1 wt and 58 L1 R transcripts (see EXAMPLE 4). The blot was probed with a cocktail of equal amounts of DIG-labeled 58L1 wt and 58 L1 R DNA probes. The quantity of total RNA electrophoresed per lane is indicated. The arrow on the right indicates the predicted size of a full length 58 L1 transcript.

The majority of cervical carcinomas are associated with infections of specific oncogenic types of human papillomavirus (HPV). The present invention relates to compositions and methods to elicit or enhance immunity to the protein products expressed by genes of oncogenic HPV types. Specifically, the present invention provides polynucleotides encoding HPV58 L1, wherein the polynucleotides are codon-optimnized for high-level expression in yeast. The present invention also provides HPV58 virus-like particles (VLPs), which are produced in yeast, and discloses use of said polynucleotides and VLPs in pharmaceutical compositions and vaccines for the prevention and/or treatment of HPV-associated cancer.

A wild-type HPV58 L1 nucleotide sequence has been reported (Genbank Accession # NC_001443, see Kirii et al. *Virology* 185(1): 424-427 (1991)). The present invention provides synthetic DNA molecules encoding the HPV58 L1 protein. The synthetic molecules of the present invention comprise a sequence of codons, wherein at least some of the codons have been altered to use the codons preferred by a yeast cell for high-level expression. The synthetic molecules may be used as a coding sequence for expression of HPV58 L1 protein, which may self-assemble into VLPs. Said VLPs may be used in a VLP-based vaccine to provide effective immunoprophylaxis against papiflomavirus infection through neutralizing antibody and cell-mediated immunity. Such VLP-based vaccines are also useful for treatment of already established HPV infections.

Expression of HPV VLPs in yeast cells offers the advantages of being cost-effective and easily adapted to large-scale growth in fermenters. In addition, the yeast genome can be readily altered to ensure selection of recombinant, transformed yeast with increased growth and expression potential. However, many HPV L1 proteins, including HPV58 L1 are expressed at levels in yeast cells which are lower than what is desirable for commercial scale-up.

Accordingly, the present invention relates to HPV58 L1 gene sequences that are "optimized" for high-level expression in a yeast cellular environment.

A "triplet" codon of four possible nucleotide bases can exist in over 60 variant forms. Because these codons provide the message for only 20 different amino acids (as well as transcription initiation and termination), some amino acids can be coded for by more than one codon, a phenomenon known as codon redundancy. For reasons not completely understood, alternative codons are not uniformly present in the endogenous DNA of differing types of cells. Indeed, there appears to exist a variable natural hierarchy or "preference" for certain codons in certain types of cells. As one example, the amino acid leucine is specified by any of six DNA codons including CTA, CTC, CTG, CTT, TTA, and TTG. Exhaustive analysis of genome codon use frequencies for microorganisms has revealed endogenous DNA of *E. coli* most commonly contains the CTG leucine-specifying codon, while the DNA of yeasts and slime molds most commonly includes a TTA leucine-specifying codon. In view of this hierarchy, it is generally believed that the likelihood of obtaining high levels of expression of a leucine-rich polypeptide by an *E. coli* host will depend to some extent on the frequency of codon use. For example, it is likely that a gene rich in TTA codons will be poorly expressed in *E. coli*, whereas a CTG rich gene will probably be highly expressed in this host. Similarly, a preferred codon for expression of a leucine-rich polypeptide in yeast host cells would be TTA.

The implications of codon preference phenomena on recombinant DNA techniques are manifest, and the phenomenon may serve to explain many prior failures to achieve high expression levels of exogenous genes in successfully transformed host organisms—a less "preferred" codon may be repeatedly present in the inserted gene and the host cell machinery for expression may not operate as efficiently. This phenomenon suggests that synthetic genes which have been designed to include a projected host cell's preferred codons provide an optimal form of foreign genetic material for practice of recombinant protein expression. Thus, one aspect of this invention is an HPV58 L1 gene that is codon-optimized for high-level expression in a yeast cell. In a preferred embodiment of this invention, it has been found that the use of alternative codons encoding the same protein sequence may remove the constraints on expression of HPV58 L1 proteins by yeast cells.

In accordance with this invention, HPV58 L1 gene segments were converted to sequences having identical translated sequences but with alternative codon usage as described by Sharp and Cowe (Synonymous Codon Usage in *Saccha-*

*romyces cerevisiae. Yeast* 7: 657-678 (1991)), which is hereby incorporated by reference. The methodology generally consists of identifying codons in the wild-type sequence that are not commonly associated with highly expressed yeast genes and replacing them with optimal codons for high expression in yeast cells. The new gene sequence is then inspected for undesired sequences generated by these codon replacements (e.g., "ATTTA" sequences, inadvertent creation of intron splice recognition sites, unwanted restriction enzyme sites, high GC content, presence of transcription termination signals that are recognized by yeast, etc.). Undesirable sequences are eliminated by substitution of the existing codons with different codons coding for the same amino acid. The synthetic gene segments are then tested for improved expression.

The methods described above were used to create synthetic gene segments for HPV58 L1, resulting in a gene comprising codons optimized for high-level expression. While the above procedure provides a summary of our methodology for designing codon-optimized genes for use in HPV vaccines, it is understood by one skilled in the art that similar vaccine efficacy or increased expression of genes may be achieved by minor variations in the procedure or by minor variations in the sequence.

Accordingly, the present invention relates to a synthetic polynucleotide comprising a sequence of nucleotides encoding an HPV58 L1 protein, or a biologically active fragment or mutant form of an HPV58 L1 protein, the polynucleotide sequence comprising codons optimized for expression in a yeast host cell. Said mutant forms of the HPV58 L1 protein include, but are not limited to: conservative amino acid substitutions, amino-terminal truncations, carboxy-terminal truncations, deletions, or additions. Any such biologically active fragment and/or mutant will encode either a protein or protein fragment which at least substantially mimics the immunological properties of the HPV58 L1 protein as set forth in SEQ ID NO:2. The synthetic polynucleotides of the present invention encode mRNA molecules that express a functional HPV58 L1 protein so as to be useful in the development of a therapeutic or prophylactic HPV vaccine.

One aspect of this invention is a codon-optimized nucleic acid molecule which encodes the HPV58 L1 protein as set forth in SEQ ID NO:2, said nucleic acid molecule comprising a sequence of nucleotides as set forth in SEQ ID NO:1.

The present invention also relates to recombinant vectors and recombinant host cells, both prokaryotic and eukaryotic, which contain the nucleic acid molecules disclosed throughout this specification. In a preferred embodiment of this invention, the host cell is a yeast host cell.

The synthetic HPV58 DNA or fragments thereof constructed through the methods described herein may be recombinantly expressed by molecular cloning into an expression vector containing a suitable promoter and other appropriate transcription regulatory elements, and transferred into prokaryotic or eukaryotic host cells to produce recombinant HPV58 L1. Techniques for such manipulations are fully described by Sambrook et al. (*Molecular Cloning: A Laboratory Manual*; Cold Spring Harbor Laboratory, Cold Spring Harbor, N.Y., (1989); *Current Protocols in Molecular Biology*, Ausubel et al., Green Pub. Associates and Wiley-Interscience, New York (1988); *Yeast Genetics: A Laboratory Course Manual*, Rose et al., Cold Spring Harbor Laboratory, Cold Spring Harbor, N.Y., (1990)), which are hereby incorporated by reference in their entirety.

Thus, the present invention relates to a process for expressing an HPV58 L1 protein in a recombinant host cell, comprising: (a) introducing a vector comprising a nucleic acid encoding an HPV58 L1 protein into a yeast host cell; and (b) culturing the yeast host cell under conditions which allow expression of said HPV58 L1 protein.

The present invention further relates to a process for expressing an HPV58 L1 protein in a recombinant host cell, comprising: (a) introducing a vector comprising a nucleic acid encoding an HPV58 L1 protein into a yeast host cell; wherein the nucleic acid molecule is codon-optimized for optimal expression in the yeast host cell and; (b) culturing the yeast host cell under conditions which allow expression of said HPV58 L1 protein.

This invention further relates to a process for expressing an HPV58 L1 protein in a recombinant host cell, comprising: (a) introducing a vector comprising a nucleic acid as set forth in SEQ ID NO:1 into a yeast host cell; and, (b) culturing the yeast host cell under conditions which allow expression of said HPV58 L1 protein.

The synthetic genes of the present invention can be assembled into an expression cassette that comprises sequences designed to provide efficient expression of the HPV58 L1 protein in the host cell. The cassette preferably contains the synthetic gene, with related transcriptional and translations control sequences operatively linked to it, such as a promoter, and termination sequences. In a preferred embodiment, the promoter is the *S. cerevisiae* GAL1 promoter, although those skilled in the art will recognize that any of a number of other known yeast promoters such as the GAL10, GAL7, ADH1, TDH3 or PGK promoters, or other eukaryotic gene promoters may be used. A preferred transcriptional terminator is the *S. cerevisiae* ADH1 terminator, although other known transcriptional terminators may also be used. The combination of GAL1 promoter—ADH1 terminator is particularly preferred.

This invention further provides an isolated and purified HPV58 L1 polypeptide comprising a sequence of amino acids as set forth in SEQ ID NO:2.

Another aspect of this invention is an HPV58 virus-like particle (VLP) produced by recombinantly expressing the HPV58 L1 or L1+L2 genes in a yeast cell, methods of producing HPV58 VLPs, and methods of using HPV58 VLPs. VLPs can self-assemble when L1, the major capsid protein of human and animal papillomaviruses, is expressed in yeast, insect cells, mammalian cells or bacteria (for review, see Schiller and Roden, in *Papillomavirus Reviews: Current Research on Papillomaviruses*; Lacey, ed. Leeds, UK: Leeds Medical Information, pp 101-12 (1996)). Morphologically indistinct HPV VLPs can also be produced by expressing a combination of the L1 and L2 capsid proteins. VLPs are composed of 72 pentamers of L1 in a T=7 icosahedral structure (Baker et al., *Biophys. J.* 60(6): 1445-56 (1991)).

VLPs are morphologically similar to authentic virions and are capable of inducing high titres of neutralizing antibodies upon administration into an animal. Immunization of rabbits (Breitburd et al., *J. Virol.* 69(6): 3959-63 (1995)) and dogs (Suzich et al., *Proc. Natl. Acad. Sci. USA* 92(25): 11553-57 (1995)) with VLPs was shown to both induce neutralizing antibodies and protect against experimental papillomavirus infection. However, because the VLPs do not contain the potentially oncogenic viral genome and can self-assemble when expressed from a single gene, they present a safe alternative to the use of live virus in HPV vaccine development (for review, see Schiller and Hidesheim, *J. Clin. Virol.* 19: 67-74 (2000)).

Thus, the present invention relates to virus-like particles comprised of recombinant L1 protein or recombinant L1+L2 proteins of HPV58, wherein the recombinant protein is expressed in a yeast cell.

As stated above, in a preferred embodiment of the invention, the HPV58 VLPs are produced in yeast. In a further preferred embodiment, the yeast is selected from the group consisting of: Saccharoinyces cerevisiae, Haisenula polymorpha, Pichia pastoris, Kluyveromyces fragilis, Kluyveromyces lactis, and Schizosaccharomyces pombe.

Another aspect of this invention is an HPV58 VLP which comprises an HPV58 L1 protein produced by a codon-optimized HPV58 L1 gene. In a preferred embodiment of this aspect of the invention, the codon-optimized HPV58 L1 gene comprises a sequence of nucleotides as set forth in SEQ ID NO:1.

Yet another aspect of this invention is a method of producing HPV58 VLPs, comprising: (a) transforming yeast with a recombinant DNA molecule encoding HPV58 L1 protein or HPV58 L1+L2 proteins; (b) cultivating the transformed yeast under conditions that permit expression of the recombinant DNA molecule to produce the recombinant HPV58 protein; and (c) isolating the recombinant HPV58 protein to produce HPV58 VLPs.

In a preferred embodiment of this aspect of the invention, the yeast is transformed with a codon-optimized HPV58 L1 gene to produce HPV58 VLPs. In a particularly preferred embodiment, the codon-optiized HPV58 L1 gene comprises a sequence of nucleotides as set forth in SEQ ID NO:1.

This invention also provides a method for inducing an immune response in an animal comprising administering HPV58 virus-ike particles to the animal. In a preferred embodiment, the HPV58 VLPs are produced by a codon-optimized gene.

Yet another aspect of this invention is a method of preventing and/or treating HPV-associated cervical cancer comprising administering to a mammal a vaccine comprising HPV58 VLPs. In a preferred embodiment of this aspect of the invention, the HPV58 VLPs are produced in yeast.

This invention also relates to a vaccine comprising HPV58 virus-like particles (VLPs).

In an alternative embodiment of this aspect of the invention, the vaccine further comprises VLPs of at least one additional HPV type. In a preferred embodiment, the at least one additional HPV type is selected from the group consisting of: HPV6, HPV11, HPV16, HPV18, HPV31, HPV33, HPV35, HPV39, HPV45, HPV51, HPV52, HPV55, HPV56, HPV59, and HPV68.

In a preferred embodiment of this aspect of the invention, the vaccine further comprises HPV16 VLPs.

In another preferred embodiment of the invention, the vaccine further comprises HPV16 VLPs and HPV18 VLPs.

In yet another preferred embodiment of the invention, the vaccine further comprises HPV6 VLPs, HPV11 VLPs, HPV16 VLPs and HPV18 VLPs.

This invention also relates to pharmaceutical compositions comprising HPV 58 virus-like particles. Further, this invention relates to pharmaceutical compositions comprising HPV58 VLPs and VLPs of at least one additional HPV type. In a preferred embodiment, the at least one additional HPV type is selected from the group consisting of: HPV6, HPV11, HPV16, HPV18, HPV31, HPV33, HPV35, HPV39, HPV45, HPV51, HPV52, HPV55, HPV56, HPV59, and HPV68.

Vaccine compositions of the present invention may be used alone at appropriate dosages which allow for optimal inhibition of HPV58 infection with minimal potential toxicity. In addition, co-administration or sequential administration of other agents may be desirable.

The amount of virus-like particles to be introduced into a vaccine recipient will depend on the immunogenicity of the expressed gene product. In general, an immunologically or prophylactically effective dose of about 10 µg to 100 µg, and preferably about 20 µg to 60 µg of VLPs is administered directly into muscle tissue. Subcutaneous injection, intradermal introduction, impression though the skin, and other modes of administration such as intraperitoneal, intravenous, or inhalation delivery are also contemplated. It is also contemplated that booster vaccinations may be provided. Parenteral administration, such as intravenous, intramuscular, subcutaneous or other means of administration with adjuvants such as alum or Merck aluminum adjuvant, concurrently with or subsequent to parenteral introduction of the vaccine of this invention is also advantageous.

All publications mentioned herein are incorporated by reference for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

EXAMPLE 1

Determination of a Representative HPV58 L1 Sequence

The HPV58 L1 sequence has been described previously (Genbank Accession # NC_001443). It is not uncommon, however, to find minor sequence variations between DNAs obtained from clinical isolates. To determine a representative HPV58 L1 wild-type sequence, DNA was isolated from three clinical samples previously shown to contain HPV58 DNA. HPV58 L1 sequences were amplified in a polymerase chain reaction (PCR) using Taq DNA polymerase and the following primers: HPV58 L1 F 5'-ATGTCCGTGTGGCGGCCTAGT-3' (SEQ ID NO:4) and 58 3'11 BglII 5'-GAGATCTGTG-TAAGTACCACAACAATTA-3' (SEQ ID NO:5). The amplified products were electrophoresed on agarose gels and visualized by ethidium bromide staining. The ~1500 bp L1 bands were excised and DNA purified using Geneclean Spin Kit (Q-Bio Gene, Carlsbad, Calif.). The DNA was then ligated to the TA cloning vector, pCR2.1 (Invitrogen). TOP10F' E. Coli were transformed with the ligation mixture and plated on LB agar with ampicillin plus IPTG and X-gal for blue/white colony selection. The plates were inverted and incubated for 16 hours at 37° C. White colonies were cultured in LB medium with ampicillin by shaking at 37° C. for 16 hours. Minipreps were performed to extract the plasmid DNA.

To demonstrate the presence of the L1 gene in the plasmids, restriction endonuclease digestions were conducted. Restriction fragments were viewed by agarose gel electrophoresis and ethidium bromide staining. DNA sequencing was performed on plasmids containing cloned L1 inserts from each of the three clinical isolates. In order to generate a reference sequence for later optimization, the nucleotide and translated amino acid sequences from each of the clones were compared to the published HPV58 L1 sequences. Sequence analysis of the three clinical isolates revealed that no sequence was identical to the Genbank sequence. The pCR2.1 HPV58L1 clone #4 was chosen to be the representative 58 L1 sequence and is referred to interchangeably herein as the "58 L1 wild-type sequence" or "58 wt sequence" (SEQ ID NO:3, see FIG. 1). The 58 L1 wt sequence contained five point mutations: two resulting in amino acids changes and three silent point mutations. The point mutations resulting in amino acid changes with respect to the Genbank HPV58 L1 sequence were located at nucleotide 372 (A→T), altering amino acid 124 from leucine to phenylalanine, and nucleotide 897 (A→G), altering amino acid 299 from isoleucine to methionine. The three silent point mutations were located at nucleotides 774 (A→G), 792 (T→C), and 999 (G→A).

The 58 L1 wild-type sequence was PCR-amplified using Taq polymerase and the following primers, which add BamHI extensions: 5'58 BamHI 5'-GGGATCCCACAAAA-CAAAATGTCCGTGTGGC-3' (SEQ ID NO:6) and 3'Bam 58 5'-GGGATCCGTGTAAGTACCACAACAATTA-3'(SEQ ID NO: 7). The resulting PCR products were visualized by agarose gel electrophoresis, followed by ethidium bromide staining. The ~1500 bp band was excised and DNA-purified using the Geneclean kit. The PCR product was then ligated to pCR2.1 and TOP10F' cells were transformed with the ligation mixture. White colonies were selected and cultured in LB medium with ampicillin by shaking at 37° C. for 16 hours. Minipreps were performed to extract the plasmid DNA. To release the HPV58 L1 gene from the vector sequences, BamHI restriction endonuclease digestions were performed. The digested DNA was subjected to agarose gel electrophoresis and viewed by ethidium bromide staining. The L1 band was purified using the Geneclean kit and ligated to dephosphorylated, BanHI digested pGAL110. DH5α $E$ $coli$ cells were transformed with the ligation mixture. To screen for the HPV58 L1 insert in the correct orientation, plasmid DNA from colonies was PCR-amplified. DNA sequencing was conducted to confirm sequence and orientation of the inserts. A single clone was selected and named pGAL110-HPV58L1 #10. Maxiprep DNA from the selected clone was prepared. $Saccharomyces$ $cerevisiae$ cells were made competent by spheroplasting with glusulase and transformed with pGAL110-HPV58L1 #1. The yeast transformation mixture was plated in Leu(−) sorbitol top-agar onto Leu(−) sorbitol agar plates and incubated inverted for 3-5 days at 30° C. Colonies were picked and streaked for isolation on Leu(−) sorbitol agar plates. Isolated colonies were subsequently grown in 5 ml of 5×Leu(−) Ade(−) sorbitol with 1.6% glucose and 4% galactose in rotating tube cultures at 30° C. to induce 58 L1 transcription and protein expression.

EXAMPLE 2

Yeast Codon Optimization

Yeast-preferred codons have been described (Sharp, Paul M and Cowe, Elizabeth. Synonymous Codon Usage in $Saccharomyces$ $cerevisiae$ YEAST 7: 657-678 (1991)). Expression of the HPV58 L1 wt protein was detectable, however to obtain increased expression, the HPV58 L1 gene was rebuilt utilizing the preferred yeast codons. The rebuilt 58 L1 sequence, which comprises yeast-optimized codon sequences, contained 404 nucleotide alterations compared to the 58 L1 wt sequence. The resulting sequence is referred to herein as "58 L1 R" (R=rebuild, see FIG. 1). The translated amino acid sequence of 58 L1 R was not altered. The nucleotide (SEQ ID NO:1) and amino acid (SEQ ID NO:2) sequences of HPV58 L1 R are shown in FIG. 2. Said rebuilt sequence provides increased HPV58 L1 expression, which is a significant advance over the wild-type for use in vaccine development (see EXAMPLE 4).

The strategy employed to produce the optimized gene was to design long overlapping sense and antisense oligomers that span the gene, substituting nucleotides with yeast-preferred codon sequences, while maintaining the amino acid sequence. These oligomers were used in place of template DNA in a PCR reaction with Pfu polymerase. Additional amplification primers were designed and used to amplify the rebuilt sequences from template oligomers.

The optimal conditions for amplification were section-specific, however, most employed a program resembling 95° C. for 2 minutes (denaturing) followed by 35 cycles of 95° C. for 1 minute (denaturing), 55° C. for 1 minute (annealing), 72° C. for 3.5 minute (extension), followed by a 72° C. for 10 minute final extension and 4° C. hold. PCR products were examined by agarose gel electrophoresis. Bands of the appropriate size were excised and DNA gel purified. The amplified fragments were then used as templates to assemble the 1497 nt rebuilt HPV58 L1 gene.

Following rebuild, the 1497 nt band was gel purified and ligated to pCR-Blunt vector (Invitrogen, Carlsbad, Calif.). Following ligation, TOP10 cells were transformed with the ligation mixture. Colonies were grown in LB with kanamycin and plasmid DNA was extracted from the colonies by miniprep techniques. The plasmid DNA was sequenced to confirm the desired 58 L1 rebuild changes. To add BamHI extensions to both ends, the 58 L1 R (rebuild) was re-amplified from pCR-Blunt-58 L1 R with the following primers: 5'Bam 58Rebuild5'-GGATCCCACAAAACAAAATGTCT-GTCTGGAGACC-3' (SEQ ID NO:8) and 3'Bam 58 Rebuild 5'-GGATCCTTACTTCTTGACCTTC-3' (SEQ ID NO:9).

The amplified L1 product was gel-purified using the Geneclean kit and cloned into pCR2.1 (Invitrogen). Top10F cells were transformed with the pCR2.1 plasmid. White colonies were cultured in LB medium with ampicillin, shaking at 37° C. for 16 hours. Minipreps were performed to extract the plasmid DNA. To release the HPV58 L1 gene from the vector sequences, BamHI restriction endonuclease digestions were performed. The digested DNA was subjected to agarose gel electrophoresis and viewed by ethidium bromide staining. The L1 band was purified using the Geneclean kit and ligated to dephosphorylated, BamHI-digested pGAL110. DH5α $E$. $coli$ cells were transformed with the ligation mixture.

The resulting colonies were screened by PCR for the HPV58 L1 insert in the correct orientation. Maxiprep DNA was prepared. Sequence and orientation were confirmed by restriction digest profiles and DNA sequencing. The selected clone was named pGAL 110-HPV58L1R #17. $Saccharomyces$ $cerevisiae$ cells were made competent by spheroplasting and transformed with pGAL110-HPV58L1R #17. The yeast transformation was plated in Leu(−) sorbitol top-agar on Leu (−) sorbitol agar plates and incubated inverted for 3-5 days at 30° C. Colonies were picked and streaked for clonal isolation on Leu(−) sorbitol agar plates. Isolated colonies were subsequently grown in 5 ml of 5×Leu(−) Ade(−) sorbitol with 1.6% glucose and 4% galactose in rotating tube cultures at 30° C. to induce L1 transcription and protein expression. After 48 hours, a culture volume equivalent to an $OD_{600}=10$ amount of cells was pelleted, the supernatant was removed and the pellets were frozen and stored at −70° C.

EXAMPLE 3

RNA Preparation

Cell pellets of transformed yeast cells induced to express HPV58 L1 or HPV 58 L1 R by galactose induction were thawed on ice, suspended in 0.8 ml of Trizol reagent (Life Technologies, Gibco BRL) and incubated at room temperature for 5 minutes. One fifth volume of chloroform was added to the vial. It was then shaken vigorously for 15 seconds to mix and incubated at room temperature for 3 minutes. After a 5 minute centrifugation at 13 k rpms, the upper phase was collected and transferred to a new vial. 0.4 ml isopropanol was added and incubated at room temperature for 10 minutes. To pellet the RNA, centrifugation was performed at 13 k rpms for 10 minutes. The supernatant was decanted, the RNA pellet washed with 75% EtOH and centrifugation repeated. The supernatant was decanted and the RNA pellet allowed to air dry for 15 minutes followed by suspension in RNase-free water. Spectrophotometry was performed to determined the concentration of RNA in the sample using the assumption that an $A_{260}$ reading of 1=40 µg/ml RNA when the $A_{260/280}$ is 1.7-2.0.

EXAMPLE 4

Northern Blot Analysis

A 1.1% agarose formaldehyde gel was cast. Five and ten micrograms of RNA were combined with denaturing buffer (final concentrations: 6% formaldehyde, 50% formamide and 0.1×MOPS) and heated to 65° C. for 10 minutes. A one-tenth volume of gel loading buffer was added and the sample loaded onto the gel. Electrophoresis was performed at 75 volts in 1×MOPS buffer for ~3 hours. The gel was washed for 60 minutes in 10×SSC.

The RNA was transferred to a Hybond-N+nylon membrane (Amersham Biosciences, Piscataway, N.J.) by capillary action over 16 hours in 10×SSC. The RNA was then fixed to the nylon membrane by cross-linking using the Stratagene UV Stratalinker auto-crosslink function (Stratagene, La Jolla, Calif.). After fixing, the nylon membrane was allowed to air dry.

The Roche DIG High Prime DNA Labeling and Detection Kit I (Hoffmann-La Roche Ltd., Basel, Switzerland) was used to label 58 L1 wt and 58 L1 R DNA sequences with DIG to be used as a probe cocktail to detect 58 L1 wt and 58 L1 R transcripts on the Northern blot. The pre-hybridization, hybridization and immunological development using an anti-DIG alkaline phosphatase conjugated antibody were performed per the manufacturer's recommendations. Briefly, the blot was pre-hybridized at 37° C. for 30 minutes with gentle shaking. The probe cocktail was denatured by heating to 95° C. for 5 minutes and quenching on ice. The probe cocktail was added to the hybridization solution and applied to the membrane for 4 hours at 44.6° C. with gentle shaking. The hybridization solution was then removed and the blot washed 2 x for 5 minutes in 2×SSC with 0.1% SDS at room temperature, followed by an additional wash at 65° C. with 0.5×SSC and 0.1% SDS. The blot was then blocked for 30 minutes and anti-DIG alkaline phosphatase conjugated antibody was applied at a 1:5000 dilution for 30 minutes. The blot was washed and the presence of probe-bound RNA was determined by NBT/BCIP substrate detection of the alkaline phosphatase conjugated anti-DIG bound antibody.

Initial analysis of yeast expressing 58 L1 wt suggested that there was functional HPV58 L1 full-length transcription and translation; however, the level of expression might be increased if the sequence was rebuilt with yeast-preferred codon sequences. The rebuilt 58 L1 sequence was engineered to omit any possible premature transcription termination sites to ensure robust transcription. Northern blot analysis of the 58 L1 R transcript revealed that increased amounts of full-length transcripts were generated compared to the results seen for 58 L1 wt (FIG. 3).

EXAMPLE 5

HPV58 L1 Protein Expression

Frozen yeast cell pellets of galactose-induced cultures equivalent to an $OD_{600}$=10 quantity of cells, were thawed on ice and suspended in 300 µl of PC buffer (100 mM Na2HPO$_4$ and 0.5 M NaCl, pH 7.0) with 2 mM PMSF. Acid-washed 0.5 mm glass beads were added at a concentration of ~0.5 g/tube. The tubes were vortexed for 3 cycles of 5 minutes at 4° C. with a 1 minute break. 7.5 µl of 20% TritonX100 was added and the vortex step was repeated for 5 minutes at 4° C. The tubes were placed on ice for 15 minutes, followed by centrifugation for 10 minutes at 4° C. The supernate was transferred to a sterile microfuge tube, labeled as total yeast protein extract, dated and stored at −70° C.

EXAMPLE 6

Western Blot Analysis

Total yeast protein extract from twenty isolated yeast colonies for each 58 L1 construct were analyzed by Western blot to confirm expression of 58 L1 protein after galactose induction.

Ten, five and two and one-half micrograms of total yeast protein extract of representative 58 L1 wt and 58 L1 R isolates were combined with SDS-PAGE loading buffer and heated to 95° C. for 10 minutes. The 16 L1 protein, which is approximately 55 kD, was included as a positive control, along with HPV L1-free total yeast protein extract as a negative control (data not shown).

The proteins were loaded onto a 10% SDS-PAGE gel and electrophoresed in Tris-Glycine buffer. After protein separation, the proteins were Western transferred from the gel to nitrocellulose and the blot was blocked in 1× diluent buffer (Kirkegaard and Perry Laboratories, Gaithersburg, Md.) for 1 hour at room temperature with rocking. The blot was washed three times and incubated at room temperature for 16 hours with yeast absorbed goat anti-trpE-HPV31 L1 serum, which cross-reacts with HPV16 and HPV58 L1 proteins. The blot was then washed three times and incubated with a 1:2500 dilution of anti-goat-HRP conjugated antibody for 1 hr. The blot was again washed three times and NBT/BCIP detection substrate applied (Kirkegaard and Perry Laboratories). Immunoreactive proteins were detected as purple bands on the blot.

Figure 4:
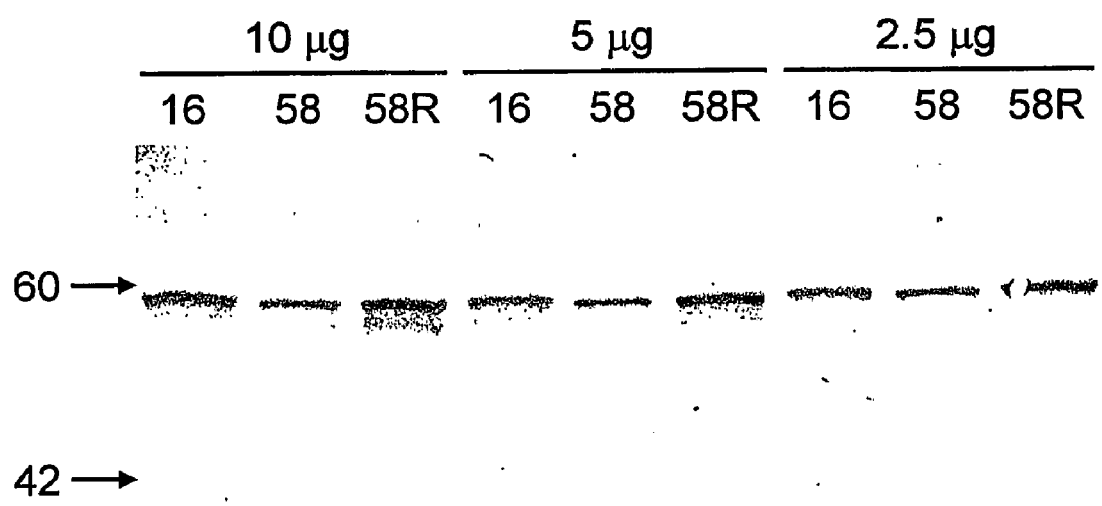
FIG. 4 shows a Western Blot of HPV58 L1 wt (58), and 58 L1 R (58R) proteins. HPV16 L1 was included as a reference (16). Ten, five and two and one-half micrograms of total yeast protein extract were denatured and applied to a 10% SDS-PAGE gel. HPV58 L1 protein was detected using a yeast-absorbed anti-trpE-HPV31 L1 goat polyclonal antiserum which cross-reacts with 58 L1 and 16 L1. Molecular weight markers are indicted in kDa on the left

In all cases, the 58 L1 protein was detected as a distinct immunoreactive band on the nitrocellulose corresponding to approximately 55 kD (FIG. 4). The intensity of the 58 L1 R bands appeared to be greater than that seen for 58 L1 wt, suggesting improved 58 L1 expression was achieved by yeast-codon optimrization.

EXAMPLE 7

ELISA Assay

To demonstrate 58 L1 VLP expression, a portion of 58 L1 wt and 58 L1 R total yeast protein extract was analyzed by ELISA. The yeast cells expressing HPV58 L1 and HPV58 L1 R were grown by a variety of methods, including rotating tube cultures, shake flasks, and fermenters. The yeast cells were lysed and protein extracts were made to determine the amount of HPV58 L1 virus-like particles (VLPs) produced per microgram of total protein. A sandwich ELISA was designed to demonstrate HPV58 L1 VLP expression.

Protein G purified H582C3.F7 (P7) monoclonal antibody (mAb) was used to bind intact 58 L1 VLPs found in the yeast protein extracts. F7 specifically recognizes an HPV58 L1 VLP conformational epitope. The unbound proteins were washed away and H586E11.F4 (F4), another HPV58 L1 VLP conformational specific mnAb, was applied as a detection antibody. True, conformationally correct, 58 L1 VLPs were bound and detection was facilitated by the use of an anti-mouse IgG2b HRP-conjugated antibody and TMB substrate.

Specifically, F7 was used to coat the bottom of Immulon 4 HBX 96 well plates overnight at 4° C. The plates were washed three times with PBS and 0.05% Tween 20, followed by blocking with blocking solution (PBS+0.05% Tween 20+1% BSA). The plates were washed three times and antigens (total yeast cell lysates diluted in blocking solution to 12.5 µg/ml) were applied to row A in duplicate. Reference standards of purified HPV58 L1 VLPs were applied to row A columns 3 and 4 at 206 ng/ml in 12.5 µg/ml total yeast protein. The reference and test samples were then serially diluted two-fold down each column. After three hours at room temperature, the excess antigen was removed by aspiration and the plates were washed 3 times. F4 conformational specific mAb was diluted in blocking solution and applied to each well for one hour at room temperature. The plates were washed three times and an anti-mouse IgG2b HRP-conjugated antibody was diluted in blocking solution and applied for 1 hour at room temperature. The plates were washed and TMB (Pierce Biotechnology, Inc., Rockford, Ill.) was applied for 5 minutes to detect HRP-conjugated antibody complexes. The detection reaction was stopped with the addition of 2M $H_2SO_4$. Plates were read at 450 nm wavelength and the concentration of HPV58 L1 VLP was determined by comparison to the reference standards in ng VLP/µg total protein.

Figure 5:
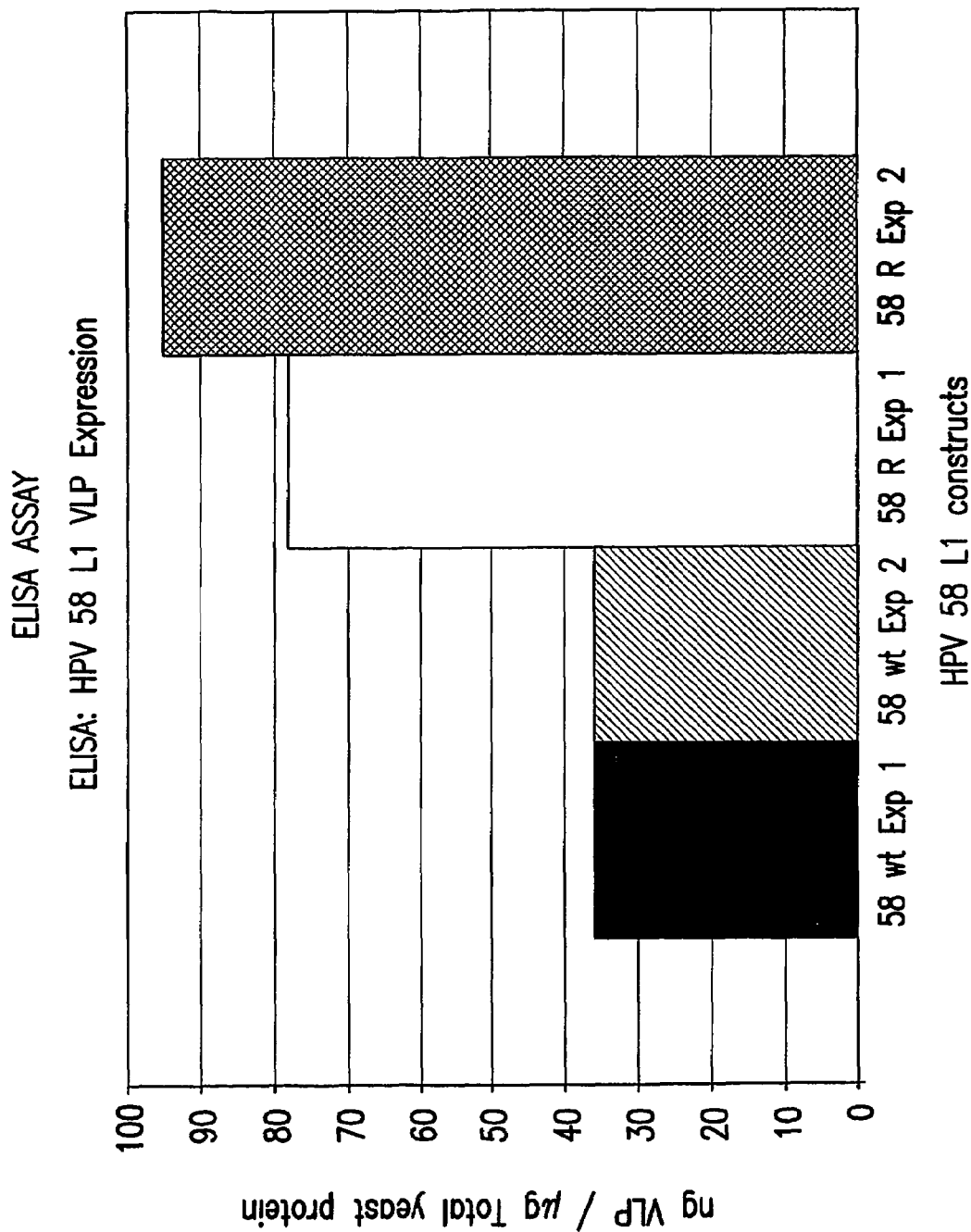
FIG. 5 depicts the amount (ng) of intact HPV58 L1 VLPs per microgram of total yeast protein captured and detected in an ELISA (see EXAMPLE 7). The results of two experiments conducted in duplicate are included. VLP expression of HPV58 L1 wt (black and gray boxes) was 36 ng/µg total yeast protein. VLP expression of HPV58 L1 R (white and hatched boxes), the rebuilt yeast-codon optimized 58 L1, was ~2-3 fold higher than HPV58 L1 wt expression reaching 95 ng/µg total yeast protein in experiment #2.

FIG. 5 shows a comparison of the amount of VLPs detected/µg of total protein from yeast expressing HPV58 L1 wt and HPV58 L1 R from two separate experiments. HPV58 L1 VLP expression levels increased ~2-3 fold with yeast-codon optimization

EXAMPLE 8

Transmission Electron Microscopy

To demonstrate that the 58 L1 protein was in fact self-assembling to form pentameric-L1 capsomers, which in turn self-assemble into virus-like particles, a partially purified 58 L1 R protein extract was subjected to transmission electron microscopy (EM).

Yeast were grown under small scale fermentation and pelleted. The resulting pellets were subjected to purification treatments. Pellet and clarified yeast extracts were analyzed by immunoblot to demonstrate L1 protein expression and retention through the purification procedure. Clarified yeast extracts were then subjected to centrifugation over a 45%-sucrose cushion and the resulting pellet suspended in buffer for analysis by transmission EM.

Figure 6:
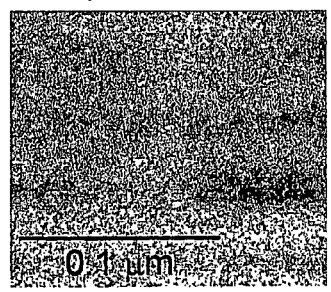
FIG. 6 shows a representative sample of HPV58 VLPs composed of HPV58 L1 R protein molecules, described herein, as visualized by transmission electron microscopy (see EXAMPLE 8). The bar represents approximately 100 nm.

A representative image of the 58 L1 R VLPs produced is shown in FIG. 6. The diameter of the spherical particles in this crude sample ranged from 30 to 60 nm, with some particles displaying a regular array of capsomers.

What is claimed is:

1. A nucleic acid molecule encoding an HPV58 L1 protein consisting of SEQ ID NO:2, wherein said nucleic acid molecule comprises a nucleic acid sequence encoding SEQ ID NO:2 which is codon-optimized for high-level expression in a yeast cell.

2. A vector comprising the nucleic acid molecule of claim 1.

3. A host cell comprising the vector of claim 2.

4. The host cell of claim 3, wherein the host cell is a yeast cell.

5. The host cell of claim 4, wherein the yeast cell is selected from the group consisting of: *Saccharomyces cerevisiae, Hansenula polymorpha, Pichia pastoris, Kluyveromyces fragilis, Kluyveromyces lactis,* and *Schizosaccharomyces pombe*.

6. The host cell of claim 5, wherein the host cell is *Saccharomyces cerevisiae*.

7. The nucleic acid molecule of claim 1, wherein the sequence of nucleotides comprises a sequence of nucleotides as set forth in SEQ ID NO:1.

8. A vector comprising the nucleic acid molecule of claim 7.

9. A host cell comprising the vector of claim 8.

* * * * *

SEQUENCE LISTING

<160> NUMBER OF SEQ ID NOS: 10

<210> SEQ ID NO 1
<211> LENGTH: 1497
<212> TYPE: DNA
<213> ORGANISM: Artificial Sequence
<220> FEATURE:
<223> OTHER INFORMATION: HPV58 L1-R

<400> SEQUENCE: 1

```
atgtccgtct ggagaccatc cgaagctacc gtctacttgc caccagttcc agtctccaag      60
gtcgtctcca ctgacgaata cgtctctaga acctctatct actactacgc tggttcctct     120
agattgttgg ctgttggtaa cccatacttc tccatcaagt ctccaaacaa caacaagaag     180
gtcttggttc caaaggtctc tggtttgcaa tacagagtct tcagagtcag attgccagac     240
ccaaacaagt tcggtttccc agacacttcc ttctacaacc cagacactca aagattggtc     300
tgggcttgtg tcggtttgga aatcggtaga ggtcaaccat gggtgttgg tgtctctggt      360 cacccatact tcaacaagtt cgacgacacc gaaacctcca acagatacccc agctcaacca     420 ggttctgaca acagagaatg tttgtccatg gactacaagc aaacccaatt gtgtttgatc     480
ggttgtaagc caccaactgg tgaacactgg ggtaaggggtg ttgcttgtaa caacaacgct     540
gctgctaccg actgtccacc attggaattg ttcaactcca tcatcgaaga cggtgacatg     600
gtcgacactg gtttcggttg tatggacttc ggtaccttgc aagctaacaa gtccgacgtt     660
ccaatcgaca tctgtaactc cacctgtaag tacccagact acttgaagat ggcttctgaa     720
ccatacggtg actccttgtt cttcttcttg agaagagaac aaatgttcgt cagacacttc     780
ttcaacagag ctggtaagtt gggtgaagct gttccagacg acttgtacat caagggttct     840
```

-continued

```
ggtaacaccg ctgtcatcca atcctctgct ttcttcccaa ctccatctgg ttccatggtc      900
acctctgaat ctcaattgtt caacaagcca tactggttgc aaagagctca aggtcacaac      960
aacggtatct gttggggtaa ccaattgttc gtcactgtcg tcgacaccac tagatccact     1020
aacatgacct tgtgtaccga agtcaccaag gaaggtacct acaagaacga caacttcaag     1080
gaatacgtca gacacgtcga ggaatacgac ttgcaattcg tcttccaatt gtgtaagatc     1140
accttgactg ctgaaatcat gacctacatc cacaccatgg actctaacat cttggaagac     1200
tggcaattcg gtttgactcc accaccatct gcttccttgc aagacaccta cagattcgtc     1260
acctctcaag ctatcacctg tcaaaagact gctccaccaa aggaaaagga agacccattg     1320
aacaagtaca ccttctggga agtcaacttg aaggaaaagt ctctgctga cttggaccaa      1380 ttcccattgg gtagaaagtt cttgttgcaa tctggtttga aggctaagcc aagattgaag     1440
agatctgctc caaccactag agctccatcc accaagagaa agaaggtcaa gaagtaa        1497
```

<210> SEQ ID NO 2
<211> LENGTH: 498
<212> TYPE: PRT
<213> ORGANISM: Human Papillomavirus Type 58

<400> SEQUENCE: 2

```
Met Ser Val Trp Arg Pro Ser Glu Ala Thr Val Tyr Leu Pro Pro Val
  1               5                  10                  15

Pro Val Ser Lys Val Val Ser Thr Asp Glu Tyr Val Ser Arg Thr Ser
                 20                  25                  30

Ile Tyr Tyr Tyr Ala Gly Ser Ser Arg Leu Leu Ala Val Gly Asn Pro
             35                  40                  45

Tyr Phe Ser Ile Lys Ser Pro Asn Asn Asn Lys Val Leu Val Pro
         50                  55                  60

Lys Val Ser Gly Leu Gln Tyr Arg Val Phe Arg Val Arg Leu Pro Asp
 65                  70                  75                  80

Pro Asn Lys Phe Gly Phe Pro Asp Thr Ser Phe Tyr Asn Pro Asp Thr
                 85                  90                  95

Gln Arg Leu Val Trp Ala Cys Val Gly Leu Glu Ile Gly Arg Gly Gln
            100                 105                 110

Pro Leu Gly Val Gly Val Ser Gly His Pro Tyr Phe Asn Lys Phe Asp
        115                 120                 125

Asp Thr Glu Thr Ser Asn Arg Tyr Pro Ala Gln Pro Gly Ser Asp Asn
    130                 135                 140

Arg Glu Cys Leu Ser Met Asp Tyr Lys Gln Thr Gln Leu Cys Leu Ile
145                 150                 155                 160

Gly Cys Lys Pro Pro Thr Gly Glu His Trp Gly Lys Gly Val Ala Cys
                165                 170                 175

Asn Asn Asn Ala Ala Ala Thr Asp Cys Pro Pro Leu Glu Leu Phe Asn
            180                 185                 190

Ser Ile Ile Glu Asp Gly Asp Met Val Asp Thr Gly Phe Gly Cys Met
        195                 200                 205

Asp Phe Gly Thr Leu Gln Ala Asn Lys Ser Asp Val Pro Ile Asp Ile
    210                 215                 220

Cys Asn Ser Thr Cys Lys Tyr Pro Asp Tyr Leu Lys Met Ala Ser Glu
225                 230                 235                 240

Pro Tyr Gly Asp Ser Leu Phe Phe Leu Arg Arg Glu Gln Met Phe
                245                 250                 255

Val Arg His Phe Phe Asn Arg Ala Gly Lys Leu Gly Glu Ala Val Pro
```

```
              260               265                270
Asp Asp Leu Tyr Ile Lys Gly Ser Gly Asn Thr Ala Val Ile Gln Ser
        275                 280                 285
Ser Ala Phe Phe Pro Thr Pro Ser Gly Ser Met Val Thr Ser Glu Ser
290                 295                 300
Gln Leu Phe Asn Lys Pro Tyr Trp Leu Gln Arg Ala Gln Gly His Asn
305                 310                 315                 320
Asn Gly Ile Cys Trp Gly Asn Gln Leu Phe Val Thr Val Val Asp Thr
                325                 330                 335
Thr Arg Ser Thr Asn Met Thr Leu Cys Thr Glu Val Thr Lys Glu Gly
        340                 345                 350
Thr Tyr Lys Asn Asp Asn Phe Lys Glu Tyr Val Arg His Val Glu Glu
        355                 360                 365
Tyr Asp Leu Gln Phe Val Phe Gln Leu Cys Lys Ile Thr Leu Thr Ala
        370                 375                 380
Glu Ile Met Thr Tyr Ile His Thr Met Asp Ser Asn Ile Leu Glu Asp
385                 390                 395                 400
Trp Gln Phe Gly Leu Thr Pro Pro Ser Ala Ser Leu Gln Asp Thr
                405                 410                 415
Tyr Arg Phe Val Thr Ser Gln Ala Ile Thr Cys Gln Lys Thr Ala Pro
        420                 425                 430
Pro Lys Glu Lys Glu Asp Pro Leu Asn Lys Tyr Thr Phe Trp Glu Val
        435                 440                 445
Asn Leu Lys Glu Lys Phe Ser Ala Asp Leu Asp Gln Phe Pro Leu Gly
        450                 455                 460
Arg Lys Phe Leu Leu Gln Ser Gly Leu Lys Ala Lys Pro Arg Leu Lys
465                 470                 475                 480
Arg Ser Ala Pro Thr Thr Arg Ala Pro Ser Thr Lys Arg Lys Val
                485                 490                 495
Lys Lys

<210> SEQ ID NO 3
<211> LENGTH: 1497
<212> TYPE: DNA
<213> ORGANISM: Human Papillomairus Type 58

<400> SEQUENCE: 3
atgtccgtgt ggcggcctag tgaggccact gtgtacctgc ctcctgtgcc tgtgtctaag      60
gttgtaagca ctgatgaata tgtgtcacgc acaagcattt attattatgc tggcagttcc     120
agacttttgg ctgttggcaa tccatatttt tccatcaaaa gtcccaataa caataaaaaa     180
gtattagttc ccaaggtatc aggcttacag tatagggtct ttagggtgcg tttacctgat     240
cccaataaat ttggttttcc tgatacatct ttttataacc ctgatacaca acgtttggtc     300
tgggcatgtg taggccttga aataggtagg gacagccat gggtgttgg cgtaagtggt     360
catccttatt tcaataaatt tgatgacact gaaaccagta acagatatcc cgcacagcca     420
gggtctgata caggaatg cttatctatg gattataaac aaacacaatt atgtttaatt     480
ggctgtaaac ctcccactgg tgagcattgg ggtaaggtg ttgcctgtaa caataatgca     540
gctgctactg attgtcctcc attgaactt tttaattcta ttattgagga tggtgacatg     600
gtagatacag ggtttggatg catggacttt ggtacattgc aggctaataa agtgatgtg     660
cctattgata tttgtaacag tacatgcaaa tatccagatt atttaaaat ggccagtgaa     720
ccttatgggg atagtttgtt ctttttctct agacgtgagc agatgtttgt taggcacttt     780
```

-continued

```
tttaataggg ccggaaaact tggcgaggct gtcccggatg acctttatat taaagggtcc    840
ggtaatactg cagttatcca aagtagtgca ttttttccaa ctcctagtgg ctctatggtt    900
acctcagaat cacaattatt taataagcct tattggctac agcgtgcaca aggtcataac    960
aatggcattt gctggggcaa tcagttattt gttaccgtag ttgataccac tcgtagcact   1020
aatatgacat tatgcactga agtaactaag gaaggtacat ataaaaatga taattttaag   1080
gaatatgtac gtcatgttga agaatatgac ttacagtttg ttttttcagct ttgcaaaatt   1140 acactaactg cagagataat gacatatata catactatgg attccaatat tttggaggac   1200
tggcaatttg gtttaacacc tcctccgtct gccagtttac aggacacata tagatttgtt   1260
acctcccagg ctattacttg ccaaaaaaca gcacccccta aagaaaagga agatccatta   1320
aataaatata cttttttggga ggttaactta aaggaaaagt tttctgcaga tctagatcag   1380
tttcctttgg gacgaaagtt tttattacaa tcaggcctta aagcaaagcc cagactaaaa   1440
cgttcggccc ctactacccg tgcaccatcc accaaacgca aaaggttaa aaaataa      1497
```

```
<210> SEQ ID NO 4
<211> LENGTH: 21
<212> TYPE: DNA
<213> ORGANISM: Artificial Sequence
<220> FEATURE:
<223> OTHER INFORMATION: PCR Primer

<400> SEQUENCE: 4
atgtccgtgt ggcggcctag t                                              21

<210> SEQ ID NO 5
<211> LENGTH: 28
<212> TYPE: DNA
<213> ORGANISM: Artificial Sequence
<220> FEATURE:
<223> OTHER INFORMATION: PCR Primer

<400> SEQUENCE: 5
gagatctgtg taagtaccac aacaatta                                       28

<210> SEQ ID NO 6
<211> LENGTH: 31
<212> TYPE: DNA
<213> ORGANISM: Artificial Sequence
<220> FEATURE:
<223> OTHER INFORMATION: PCR Primer

<400> SEQUENCE: 6
gggatcccac aaaacaaaat gtccgtgtgg c                                   31

<210> SEQ ID NO 7
<211> LENGTH: 28
<212> TYPE: DNA
<213> ORGANISM: Artificial Sequence
<220> FEATURE:
<223> OTHER INFORMATION: PCR Primer

<400> SEQUENCE: 7
gggatccgtg taagtaccac aacaatta                                       28

<210> SEQ ID NO 8
<211> LENGTH: 34
<212> TYPE: DNA
<213> ORGANISM: Artificial Sequence
<220> FEATURE:
```

<223> OTHER INFORMATION: PCR Primer

<400> SEQUENCE: 8
ggatcccaca aaacaaaatg tctgtctgga gacc                                34

<210> SEQ ID NO 9
<211> LENGTH: 34
<212> TYPE: DNA
<213> ORGANISM: Artificial Sequence
<220> FEATURE:
<223> OTHER INFORMATION: PCR Primer

<400> SEQUENCE: 9
ggatcccaca aaacaaaatg tctgtctgga gacc                                34

<210> SEQ ID NO 10
<211> LENGTH: 1497
<212> TYPE: DNA
<213> ORGANISM: Artificial Sequence
<220> FEATURE:
<223> OTHER INFORMATION: HPV 58 L1 antisense

<400> SEQUENCE: 10
tacaggcaga cctctggtag gcttcgatgg cagatgaacg gtggtcaagg tcagaggttc        60
cagcagaggt gactgcttat gcagagatct tggagataga tgatgatgcg accaaggaga       120
tctaacaacc gacaaccatt gggtatgaag aggtagttca gaggtttgtt gttgttcttc       180
cagaaccaag gtttccagag accaaacgtt atgtctcaga agtctcagtc taacggtctg       240
ggtttgttca agccaagggt tctgtgaagg aagatgttgg gtctgtgagt ttctaaccag       300
acccgaacac agccaaacct ttagccatct ccagttggta acccacaacc acagagacca       360
gtgggtatga agttgttcaa gctgctgtgg cttttggaggt tgtctatggg tcgagttggt       420
ccaagactgt tgtctcttac aaacaggtac ctgatgttcg tttgggttaa cacaaactag       480
ccaacattcg gtggttgacc acttgtgacc ccattcccac aacgaacatt gttgttgcga       540
cgacgatggc tgacaggtgg taaccttaac aagttgaggt agtagcttct gccactgtac       600
cagctgtgac caaagccaac atacctgaag ccatggaacg ttcgattgtt caggctgcaa       660
ggttagctgt agacattgag gtggacattc atgggtctga tgaacttcta ccgaagactt       720
ggtatgccac tgaggaacaa gaagaagaac tcttctcttg tttacaagca gtctgtgaag       780
aagttgtctc gaccattcaa cccacttcga caaggtctgc tgaacatgta gttcccaaga       840
ccattgtggc gacagtaggt taggagacga agaagggtt gaggtagacc aaggtaccag       900
tggagactta gagttaacaa gttgttcggt atgaccaacg tttctcgagt tccagtgttg       960
ttgccataga caaccccatt ggttaacaag cagtgacagc agctgtggtg atctaggtga      1020
ttgtactgga acacatggct tcagtggttc cttccatgga tgttcttgct gttgaagttc      1080
cttatgcagt ctgtgcagct ccttatgctg aacgttaagc agaaggttaa cacattctag      1140
tggaactgac gactttagta ctggatgtag gtgtggtacc tgagattgta gaaccttctg      1200
accgttaagc caaactgagg tggtggtaga cgaaggaacg ttctgtggat gtctaagcag      1260
tggagagttc gatagtggac agttttctga cgaggtggtt cctttttcct tctgggtaac      1320
ttgttcatgt ggaagaccct tcagttgaac ttccttttca agagacgact gaacctggtt      1380
aagggtaacc catctttcaa gaacaacgtt agaccaaact tccgattcgg ttctaacttc      1440
tctagacgag gttggtgatc tcgaggtagg tggttctctt tcttccagtt cttcatt       1497